United States Patent
Zhao et al.

(10) Patent No.: US 9,416,009 B2
(45) Date of Patent: Aug. 16, 2016

(54) METHOD FOR MODIFYING ELECTRICAL PROPERTIES OF CARBON NANOTUBES

(75) Inventors: Jianwen Zhao, Singapore (SG); Lain-Jong Li, Singapore (SG); Peng Chen, Singapore (SG); Bee Eng Mary Chan, Singapore (SG)

(73) Assignee: Nanyang Technological University, Singapore (SG)

(*) Notice: Subject to any disclaimer, the term of this patent is extended or adjusted under 35 U.S.C. 154(b) by 802 days.

(21) Appl. No.: 13/380,450

(22) PCT Filed: Jun. 28, 2010

(86) PCT No.: PCT/SG2010/000238
§ 371 (c)(1),
(2), (4) Date: Mar. 16, 2012

(87) PCT Pub. No.: WO2010/151232
PCT Pub. Date: Dec. 29, 2010

(65) Prior Publication Data
US 2012/0171103 A1    Jul. 5, 2012

Related U.S. Application Data

(60) Provisional application No. 61/220,758, filed on Jun. 26, 2009.

(51) Int. Cl.
*C07C 255/46* (2006.01)
*C07C 253/30* (2006.01)
(Continued)

(52) U.S. Cl.
CPC ............. *C01B 31/0273* (2013.01); *B82Y 10/00* (2013.01); *B82Y 30/00* (2013.01); *B82Y 40/00* (2013.01);
(Continued)

(58) Field of Classification Search
CPC ........ B82Y 10/00; B82Y 30/00; B82Y 40/00; C01B 31/0273; C01B 2202/22; G01N 27/4146; H01L 51/0049; H01L 51/002; H01M 4/625

USPC ........ 423/447.1–447.3, 445 B; 977/742–754, 977/842–848; 428/367
See application file for complete search history.

(56) References Cited

U.S. PATENT DOCUMENTS

2003/0215380 A1* 11/2003 Yang et al. .................... 423/461
2006/0024871 A1   2/2006 Balasubramanian et al.
(Continued)

FOREIGN PATENT DOCUMENTS

KR    2008-0096126 A    10/2008
WO    WO 2005/113434 A1   12/2005
WO    WO 2007/098578 A1    9/2007

OTHER PUBLICATIONS

An, L. et al., *A Simple Chemical Route to Selectively Eliminate Metallic Carbon Nanotubes in Nanotube Network Devices*, J. Am. Chem. Soc. 126 (2004) 10520-10521.
(Continued)

*Primary Examiner* — Daniel C McCracken

(57) ABSTRACT

The invention relates to a method of modifying electrical properties of carbon nanotubes by subjecting a composition of carbon nanotubes to one or more radical initiator(s). The invention also relates to an electronic component such as field-effect transistor comprising a carbon nanotube obtained using the method of the invention. The invention also relates to the use of the modified carbon nanotubes in conductive and high-strength nanotube/polymer composites, transparent electrodes, sensors and nanoelectromechanical devices, additives for batteries, radiation sources, semiconductor devices (e.g. transistors) or interconnects.

13 Claims, 5 Drawing Sheets

(51) Int. Cl.

| | |
|---|---|
| C07C 17/007 | (2006.01) |
| B01J 19/10 | (2006.01) |
| B01J 19/12 | (2006.01) |
| C01B 31/26 | (2006.01) |
| C07C 1/20 | (2006.01) |
| B82Y 30/00 | (2011.01) |
| B82Y 40/00 | (2011.01) |
| C01B 31/02 | (2006.01) |
| B82Y 10/00 | (2011.01) |
| G01N 27/414 | (2006.01) |
| H01L 51/00 | (2006.01) |
| H01M 4/62 | (2006.01) |

(52) U.S. Cl.
CPC ........ *G01N 27/4146* (2013.01); *H01L 51/0049* (2013.01); *C01B 2202/22* (2013.01); *H01L 51/002* (2013.01); *H01M 4/625* (2013.01)

(56) References Cited

U.S. PATENT DOCUMENTS

| | | | |
|---|---|---|---|
| 2008/0296539 A1* | 12/2008 | Shin et al. | 252/510 |
| 2009/0123750 A1 | 5/2009 | Chen et al. | |
| 2009/0202422 A1 | 8/2009 | Kajiura et al. | |

OTHER PUBLICATIONS

Arnold, M. S. et al., *Sorting Carbon Nanotubes by Electronic Structure Using Density Differentiation*, Nature Nanotechnology, 1 (2006) 60-65.

Balasubramanian, K. et al., *A Selective Electrochemical Approach to Carbon Nanotube Field-Effect Transistors*, Nano Letters, vol. 4, No. 5 (2004) 827-830.

Balasubramanian, K. et al., *Chemically Functionalized Carbon Nanotubes*, Small 1, No. 2 (2005), 180-192.

Bahr, J. L. et al., *Functionalization of Carbon Nanotubes by Electrochemical Reduction of Aryl Diazonium Salts: A Bucky Paper Electrode*, J. Am. Chem. Soc., 123 (2001) 6536-6542.

Barson, C. A. et al., *A Tracer Study of the Benzoyloxy Radical*, Tetrahedron, vol. 4 (1958) 147-156.

Bhushan, B., *Introduction to Carbon Nanotubes, 3.4 Properties of Carbon Nanotubes*, Springer Handbook of Nanotechnology (2007) 69-79.

Cao, Q. et al., *Highly Bendable, Transparent Thin-film Transistors That Use Carbon-Nanotube-Based Conductors and Semiconductors With Elastomeric Dielectrics*, Adv. Mater. 18 (2006) 304-309.

Cao, Q. et al., *Medium-Scale Carbon Nanotube Thin-Film Integrated Circuits on Flexible Plastic Substrates*, Nature, vol. 454 (2008) 495-500.

Chen, F. et al., *Toward the Extraction of Single Species of Single-Walled Carbon Nanotubes Using Fluorene-Based Polymers*, Nano Letters, vol. 7, No. 10 (2007) 3013-3017.

Chen, J. et al., *Solution Properties of Single-Walled Carbon Nanotubes*, Science, vol. 282 (1998) 95-98.

Ding, L. et al., *Selective Growth of Well-Aligned Semiconducting Single-Walled Carbon Nanotubes*, Nano Letters, vol. 9, No. 2 (2009) 800-805.

Engel, M. et al., *Thin Film Nanotube Transistors Based on Self-Assembled, Aligned, Semiconducting Carbon Nanotube Arrays*, ACSNano, vol. 2, No. 12 (2008) 2445-2452.

Hu, L. et al., *Percolation in Transparent and Conducting Carbon Nanotube Networks*, Nano Letters, vol. 4, No. 12 (2004) 2513-2517.

Krupke, R. et al., *Thin Films of Metallic Carbon Nanotubes Prepared by Dielectrophoresis*, Adv. Mater. 18 (2006) 1468-1470.

Krupke, R. et al., *Separation of Metallic From Semiconducting Single-Walled Carbon Nanotubes*, Science, vol. 301 (2003) 344-347.

Ju, S. et al., *Enrichment Mechanism of Semiconducting Single-Walled Carbon Nanotubes by Surfactant Amines*, J. Am. Chem. Soc. 131 (2009) 6775-6784.

Ju, S. et al., *Selection of Carbon Nanotubes With Specific Chiralities Using Helical Assemblies of Flavin Mononucleotide*, Nature Nanotechnology, vol. 3 (2008) 356-362.

Kanungo, M. et al., *Suppression of Metallic Conductivity of Single-Walled Carbon Nanotubes by Cycloaddition Reactions*, Science, vol. 323 (2009) 234-237.

Lee, C. W. et al., *Toward High-Performance solution-Processed Carbon Nanotube Network Transistors by Removing Nanotube Bundles*, J. Phys. Chem. C. vol. 12, No. 32 (2008) 12089-1291.

LeMieux, M. C. et al., *Self-Sorted, Aligned Nanotube Networks for Thin-Film Transistors*, Science, vol. 321 (2008) 101-104.

Li, H. et al., *Selective Interations of Porphyrins With Semiconducting Single-Walled Carbon Nanotubes*, J. Am. Chem. Soc. 126 (2004) 1014-1015.

Li, L. et al., *The Effects of Nitrogen and Boron Doping on the Optical Emission and Diameters of Single-Walled Carbon Nanotubes*, Carbon 44 (2006) 2752-2757.

Maeda, Y. et al., *Large-Scale Separation of Metallic and Semiconducting Single-Walled Carbon Nanotubes*, J. Am. Chem. Soc. 127 (2005) 10287-10290.

Mawhinney, D. B. et al., *Infrared Spectral Evidence for the Etching of Carbon Nanotubes: Ozone Oxidation of 298 K*, J. Am. Chem. Soc. 122 (2000) 2383-2384.

McIntosh, D. et al., *Benzoyl Peroxide Initiated in Situ Functionalization, Processing, and Mechanical Properties of Single-Walled Carbon Nanotube—Polypropylene Composite Fibers*, J. Phys. Chem. C 111 (2007) 1592-1600.

Miyata, Y. et al., *Selective Oxidation of Semiconducting Single-Wall Carbon Nanotubes by Hydrogen Peroxide*, J. Phys. Chem. B, vol. 110, No. 1 (2006) 25-29.

Nish, A. et al., *Highly Selective Dispersion of Single-Walled Carbon Nanotubes Using Aromatic Polymers*, Nature Nanotechnology, vol. 2 (2007) 640-646.

Papagelis, K. et al., *Covalently Functionalized Carbon Nanotubes as Macroinitiators for Radical Polymerization*, Phys. Stat. Sol. (b) 244, No. 11 (2007) 4046-4050.

Peng, H. et al., *Sidewall Functionalization of Single-Walled Carbon Nanotubes With Organic Peroxides*, Chem. Commun. (2003) 362-363.

Rao, A. M. et al., *Effect of Van Der Waals Interactions on the Raman Modes in Single Walled Carbon Nanotubes*, Physical Review Letters, vol. 86, No. 17 (2001) 3895-3898.

Ryu, K. et al., *CMOS—Analogous Wafer-Scale Nanotube-on-Insulator Approach for Submicrometer Devices and Integrated Circuits Using Aligned Nanotubes*, Nano Letters, vol. 9, No. 1 (2009) 189-197.

Snow, E. S. et al., *Random Networks of Carbon Nanotubes as an Electronic Material*, Applied Physics Letters, vol. 82, No. 13 (2003) 2145-2147.

Strano, M. S. et al., *Assignment of (n, m) Raman and Optical Features of Metallic Single-Walled Carbon Nanotubes*, Nano Letters, vol. 3, No. 8 (2003) 1091-1096.

Strano, M. S. et al., *Electronic Structure Control of Single-Walled Carbon Nanotube Functionalization*, Science, vol. 301 (2003) 1519-1522.

Tanaka, T. et al., *Simple and Scalable Gel-Based Separation of Metallic and Semiconducting Carbon Nanotubes*, Nano Letters, vol. 9, No. 4 (2009) 1497-1500.

Topinka, M. A. et al., *Charge Transport in Interpentrating Networks of Semiconducting and Metallic Carbon Nanotubes*, Nano Letters, vol. 9, No. 5 (2009) 1866-1871.

Unalan, H. E. et al., *Design Criteria for Transparent Single-Wall Carbon Nanotube Thin-Film Transistors*, Nano Letters, vol. 6, No. 4 (2006) 677-682.

Wang, C. et al., *Electronically Selective Chemical Functionalization of Carbon Nanotubes: Correlation Between Raman Spectral and Electrical Responses*, J. Am. Chem. Soc. 127 (2005) 11460-11468.

Wang, W. et al., *Metallic Single-Walled Carbon Nanotubes of Conductive Nanocomposites*, J. Am. Chem. 130 (2008) 1415-1419.

(56) References Cited

OTHER PUBLICATIONS

Wei, L., et al., *Selective Enrichment of (6,5) and (8,3) Single-Walled Carbon Nanotubes Via Cosurfactant Extraction From Narrow (n,m) Distribution Samples*, J. Phys. Chem. B, vol. 112, No. 10 (2008) 2771-2774.

Wildöer, J. W. G. et al., *Electonic Structure of Atomically Resolved Carbon Nanotubes*, Nature, vol. 391 (1998) 59-62.

Wiltshire, J. G. et al., *Chirality-Dependent Boron-Mediated Growth of Nitrogen-Doped Single-Walled Carbon Nantubes*, Physical Review B 72 (2005) 205431-1 to 205431-6.

Zhang, G. et al., *Selective Etching of Metallic Carbon Nanotubes by Gas-Phase Reaction*, Science, vol. 314 (2006) 974-977.

Zheng, M. et al., *DNA-Assisted Dispersion and Seperation of Carbon Nanotubes*, Nature Materials, vol. 2 (2003) 338-342.

Zheng, M. et al., *Solution Redox Chemistry of Carbon Nanotubes*, J. Am. Chem. Soc. 126 (2004) 15490-15494.

Zhou, Y. et al., *p-Channel, n-Channel Thin Film Transistors and p-n Diodes Based on Single Wall Carbon Nanotubes Networks*, Nano Letters, vol. 4, No. 10(2004) 2013-2035.

\* cited by examiner

METHOD FOR MODIFYING ELECTRICAL PROPERTIES OF CARBON NANOTUBES

CROSS-REFERENCE TO RELATED APPLICATIONS

This application makes reference to and claims the benefit of priority of an application for "High yield fabrication of semiconducting thin-film transistors using single-walled carbon nanotubes chemically modified by radical initiators" filed on Jun. 26, 2009 with the United States Patent and Trademark Office, and there duly assigned Ser. No. 61/220,758. The content of said application filed on Jun. 26, 2009 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention refers to the field of carbon nanotubes, in particular chemical methods for modifying electrical properties of carbon nanotubes using radical initiators.

BACKGROUND OF THE INVENTION

Since their discovery single-walled carbon nanotubes (SWNTs) have generated much interest as one of the best candidates for electronic devices owing to their exceptional conductivity and field-effect transistor (FET) behaviour. The undesired presence of metallic nanotubes along with semiconducting nanotubes, however, is the major hurdle to obtain ideal semiconducting devices, i.e. an unsolved obstacle to the realization of the widespread applications of carbon nanotubes is the control of nanotube electronic properties.

During nanotube growth processes, the wrapping around and joining of a graphene sheet leads to many possible chiralities. With most growth processes, about a third of the nanotube species are metallic (for example, met-SWNTs) and the rest semiconducting (for example, sem-SWNTs).

For use as the FET active material, only sem-SWNTs are desired. The poor growth selectivity of sem-SWNTs and efficiency of destroying met-SWNTs make efficient post-synthesis separation schemes necessary. Various approaches have been attempted to isolate semiconducting SWNTs from metallic ones for enhancing the semiconducting characteristics of devices, including dielectrophoresis, selective oxidation, aromatic extraction, surfactant extraction, amine extraction, surface alignment, removal of nanotube bundles, selective polymer wrapping, density gradient centrifugation and selective chemical functionalization. These methods, however, are not able to produce high quality SWNT-nets with high yield or involve complicated and costly procedures. Recent studies based on density gradient ultracentrifugation (DGU) and gel-based separation techniques have demonstrated promising results for sorting SWNTs. And notably, a very recent report showed that metallic conductivity of SWNT-nets can be effectively suppressed by cycloadditive reaction (Kanungo et al., Science 2009, 323, 234-237). This method, however, relies on harsh and lengthy reaction processes. And the yield-efficiency of high performance SWNT-net from this method was not reported.

Thus it is an object of the present invention to provide alternative methods for isolating different species of carbon nanotubes.

SUMMARY OF THE INVENTION

In the first aspect the present invention relates to a method of modifying electrical properties of carbon nanotubes by subjecting a composition of carbon nanotubes to one or more radical initiator(s).

In a second aspect the present invention relates to an electronic component such as field-effect transistor comprising a carbon nanotube modified/obtained using the method of the invention.

In a third aspect the present invention relates to the use of the modified carbon nanotubes obtained by the modification method in conductive and high-strength nanotube/polymer composites, transparent electrodes, sensors and nanoelectromechanical devices, additives for batteries, radiation sources, semiconductor devices (e.g. transistors) or interconnects.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
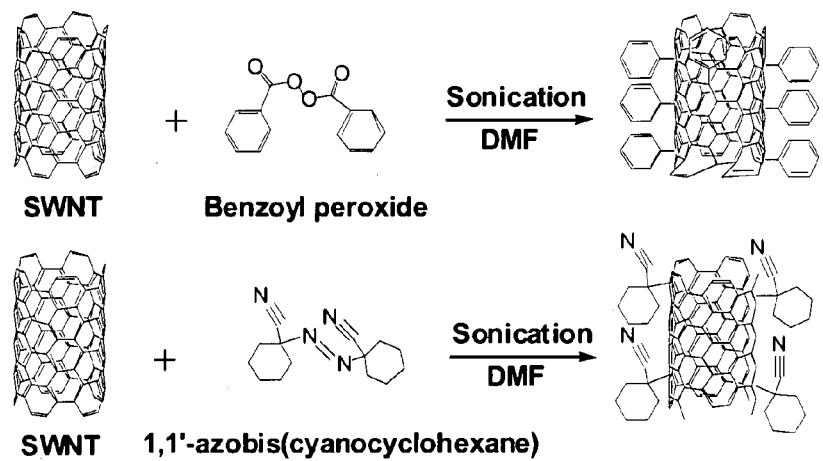
FIG. 1. shows a schematic illustration for the chemical modification of SWNTs by BPO- and ACN-derived radicals.

In the following description non-limiting embodiments of the process of the invention will be explained.

According to the present invention, it has been surprisingly found that carbon nanotubes may be modified in a simple, cost-effective, and solution processable method using radical initiators. A high yield based on the chemical modification can be obtained with every kind of radical initiator. Thus, in one embodiment the present invention refers to a method of modifying the electrical properties of carbon nanotubes by subjecting a composition of carbon nanotubes to one or more radical initiator(s). By modifying the electrical properties of carbon nanotubes improved chemical and physical characteristics may be obtained which increases the possible applications of such compounds.

Generally, a nano-structured material, such as nanotubes, refers to a material with dimensions in the nanometer range. Nano-structured materials can be classified into the following dimensional types: Zero dimensional (0D): nanospherical particles (also called nanoparticles); one dimensional (1D): nanorods, nanowires (also called nanofibers) and nanotubes; and two dimensional (2D): nanoflakes, nanoflowers, nanodiscs and nanofilms.

A carbon nanotube as used in the present invention is a cylinder of rolled up graphitic sheets. Single-, double- and multi-walled carbon nanotubes are known and can equally be used in the method of the present invention. The carbon nanotubes may be of any desired length, such as in the range from about 0.1 nm to about 10 µm, such as about 1 nm to about 5 µm or 10 nm to about 1 In one embodiment the carbon nanotubes may be at most 2 µm or between about 0.5 µm and about 2 µm or between about 1 µm and about 2 µm. The conductivity of the carbon nanotubes used may be freely selected according to any specific requirements. Depending on the arrangement of the carbon hexagon rings along the surface of the nanotubes, carbon nanotubes can be metallic or semiconducting. Any such carbon nanotubes may be used in a method according to the present invention.

Carbon nanotubes exist in different forms, such as single-walled carbon nanotubes (SWNT), double-walled carbon nanotubes (DWNT), multi-walled carbon nanotubes (MWNT), or modified multi-walled carbon nanotubes.

A single-walled carbon nanotube (SWNT) is a seamless cylinder formed from one graphite layer. For example, carbon nanotubes can be described as a graphite plane (so called graphene) sheet rolled into a hollow cylindrical shape so that the structure is one-dimensional with axial symmetry, and in general exhibiting a spiral conformation, called chirality. A single-wall nanotube can be defined by a cylindrical sheet with a diameter of about 0.7 to about 20 nm, such as about 1 to about 20 nm.

Double-walled carbon nanotubes (DWNT) consist of two layers of graphite sheets rolled in to form a tube shape. The two layers of graphite sheets can form a concentric cylinder. The nanotubes are considered as a cross between SWNT and MWNT as they can have the electronic properties of the SWNT, and the mechanical strength of MWNT. DWNT may be semi-conducting or metallic.

Multi-walled carbon nanotubes (MWNT) consist of multiple layers of graphite rolled in on to form a tube shape. The nanotubes can also exist in forms in which they have hydrophilic groups such as hydroxyl group, pyrenes, esters, thiols, amines, a carboxyl group and mixtures thereof on their surface.

In one embodiment of the invention, the carbon nanotubes are single-walled carbon nanotubes.

Carbon nanotubes may be prepared by several different methods known in the art. For example, SWNT may be grown by carbon monoxide (CO) disproportionation (decomposition into C and $CO_2$) at 700-950° C. in flow of pure CO at a total pressure that typically ranges from 1 to 10 atm using a catalyst comprising cobalt (Co) and molybdenum (Mo) on a mesoporous silica support, leading to so-called CoMoCAT® SWNTs. Using this method, diameter control of SWNTs can be achieved. Another possibility is the synthesis using high pressure carbon monoxide (HiPco) leading to so-called HiPco SWNTs. Generally, in a HiPco method, metal catalyst is formed in situ when $Fe(CO)_5$ or $Ni(CO)_4$ is injected into a reactor along with a stream of CO gas at a temperature range of about 900-1100° C. at a pressure of about 30 to 50 atm. The metal catalyst formed can be in the form of nanometer sized particles. HiPCo SWNTs are produced following the disproportionation of CO by the metal catalyst particles. In the present invention all types of SWNTs may be used for the enrichment process. In an exemplary embodiment CoMoCAT® and HiPco SWNTs were used to demonstrate the usability of the polymers described herein.

The radical initiators according to the present invention belong to the general group of compounds that can produce radical species under mild conditions. These substances generally possess weak bonds, i.e. bonds that have small bond dissociation energies. Such bonds may be easily broken to form the respective radical. Generally, every compound that may produce radical species may be used in the process of the present invention. The radical formed from the radical initiator will react with the carbon nanotube in order to produce a modified carbon nanotube. The electrical properties of the modified carbon nanotube may be significantly different to the electrical properties of the unmodified carbon nanotube.

The radical initiator may be, but is not limited to, an organic peroxide, an inorganic peroxide, an azo compound, a halogen-containing compound or a mixture thereof.

An organic peroxide according to the present invention is an organic compound containing a peroxide functional group (ROOR'), wherein R and R' may be a hydrocarbon or hydrogen with the proviso that only one of R and R' is a hydrogen. The O-O bond easily breaks and forms free radicals of the form RO'. Examples of organic peroxides may be, but are not limited to, methyl ethyl ketone peroxide, benzoyl peroxide, acetone peroxide, pinane hydroperoxide, cumene hydroperoxide, tert-butyl hydroperoxide (TBHP), 1,1-bis(tert-amylperoxy)cyclohexane, 1,1-bis(tert-butylperoxy)-3,3,5-trimethylcyclohexane, 1,1-bis(tert-butylperoxy)cyclohexane, 2,2-bis(tert-butylperoxy)butane, 2,4-pentanedione peroxide, 2,5-bis(tert-butylperoxy)-2,5-dimethylhexane, 2,5-di(tert-butylperoxy)-2,5-dimethyl-3-hexyne, 2-butanone peroxide, di-tert-amyl peroxide, tert-butylperoxy octoate, tert-butylperoxy neodecanoate, tert-butylperoxy isobutarate, dicumyl peroxide, lauroyl peroxide, tert-amylperoxy pivalate, tert-butylperoxy pivalate, tert-butyl peroxyacetate, tert-butyl peroxybenzoate, tert-butylperoxy 2-ethylhexyl carbonate or mixtures thereof. In one embodiment of the invention the organic peroxide is benzoyl peroxide (BPO). BPO can be thermally dissociated into benzoyloxy or phenyl radicals.

Examples of inorganic peroxides according to the present invention may be, but are not limited to, hydrogen peroxide, ammonium persulfate, hydroxymethanesulfinic acid monosodium salt dihydrate, potassium persulfate, sodium persulfate and mixtures thereof.

An azo compound according to the present invention is a compound bearing the functional group $R^1$—N=N—$R^2$, in which $R^1$ and $R^2$ can be either aryl or alkyl. The term "alkyl" refers to a fully saturated aliphatic hydrocarbon. In certain embodiments, alkyls are optionally substituted. In certain embodiments, an alkyl comprises 1 to 10 carbon atoms, for example 1 to 8 carbon atoms or 1 to 6 carbon atoms, wherein (whenever it appears herein in any of the definitions given below) a numerical range, such as "1 to 10" or "$C_1$-$C_{10}$", refers to each integer in the given range, e.g. "$C_1$-$C_{10}$ alkyl"

means that an alkyl group comprises only 1 carbon atom, or 2 carbon atoms, 3 carbon atoms, 4 carbon atoms, 5 carbon atoms, 6 carbon atoms, 7 carbon atoms, 8 carbon atoms, 9 carbon atoms, up to and including 10 carbon atoms. Examples of alkyl groups include, but are not limited to, methyl, ethyl, n-propyl, isopropyl, n-butyl, isobutyl, sec-butyl, tert-butyl, tert-amyl, pentyl, hexyl, heptyl, octyl, nonyl, decyl and the like. The term "aryl" refers to an aromatic ring wherein each of the atoms forming the ring is a carbon atom. The term "aromatic" refers to a group comprising a covalently closed planar ring having a delocalized [π]-electron system comprising 4n+2 [π] electrons, where n is an integer. Aryl rings may be formed by five, six, seven, eight, nine, or more than nine carbon atoms. Aryl groups may be optionally substituted. Examples of aryl groups include, but are not limited to phenyl, naphthalenyl, phenanthrenyl, anthracenyl, tetralinyl, fluorenyl, indenyl, and indanyl. In certain embodiments, an aryl group is substituted at one or more of the para, meta, and/or ortho positions.

Examples of azo compounds useful in the present invention are, but not limited to, azobenzene, diethyldiazene, azobisisobutyronitrile, 1,1'-azobis(cyanocyclohexane) (ACN), 2,2'-azobis(2-methylpropionamidine)dihydrochloride, 2,2'-azobis(2-methylpropionitrile), 4,4'-azobis(4-cyanovaleric acid), 4,4'-azobis(4-cyanovaleric acid), 2,2'-azobis(2-butanenitrile), 4,4'-azobis(4-pentanoic acid), 1,1'-azobis(cyclohexanecarbonitrile), 2-(tert-butylazo)-2-cyanopropane, 2,2'-azobis[2-methyl-N-(1,1)-bis(hydroxymethyl)-2-hydroxyethyl]propionamide, 2,2'-azobis[2-methyl-N-hydroxyethyl]propionamide, 2,2'-azobis(N,N'-dimethyleneisobutyramidine)dichloride, 2,2'-azobis(2-amidinopropane)dichloride, 2,2'-azobis(N,N'-dimethyleneisobutyramide), 2,2'-azobis(2-methyl-N-[1,1-bis(hydroxymethyl)-2-hydroxyethyl]propionamide), 2,2'-azobis(2-methyl-N-[1,1-bis(hydroxymethyl)ethyl]propionamide), 2,2'-azobis[2-methyl-N-(2-hydroxyethyl)-propionamide)], 2,2'-azobis(isobutyramide)dihydrate, or mixtures thereof.

A halogen-containing compound according to the present invention is a compound having a diatomic halogen bond. Such compounds can generate two free radicals resulting from the homolysis of the bond. Example of such halogen-containing compounds are, but not limited to, fluorine or chlorine.

It is also possible to use redox systems as radical initiators for the inventive methods. For example, redox systems may be mixtures of hydrogen peroxide, alkyl peroxide, peresters, percarbonates, and the like, and any one of the salts of iron, titanous salts, zinc formaldehyde-sulfoxylate, or sodium, formaldehyde-sulfoxylate, and reducing sugar; mixtures of persulfates, perborate or perchlorate of alkali metals or of ammonium, combined with bisulfate of an alkali metal, such as sodium metabisulfite, and reducing sugars; or mixtures of persulfate of an alkali metal combined with an arylphosphonic acid, such as benzenephosphonic acid and like compounds, and reducing agents.

In one embodiment of the invention the modification may additionally be carried out in the presence of one or more alkens(s) and/or one or more alkyne(s) or mixtures thereof. The term "alkene", alone or in combination, refers to an aliphatic hydrocarbon having one or more carbon-carbon double-bonds. In certain embodiments, alkene groups are optionally substituted. Examples of alkene groups include, but are not limited to, ethenyl, propenyl, butenyl, 1,4-butadienyl, pentenyl, hexenyl, 4-methylhex-1-enyl, 4-ethyl-2-methylhex-1-enyl and the like. The term "alkyne", alone or in combination, refers to an aliphatic hydrocarbon having one or more carbon-carbon triple-bonds. In certain embodiments, alkyne groups are optionally substituted. Examples of alkyne groups include, but are not limited to, ethynyl, propynyl, butynyl, and the like.

Without to be bound by theory, in case one or more alkene(s) and/or alkyne(s) are present in the reaction mixture, the radical formed from the radical initiator is not only reacting directly with the carbon nanotube, but may also react with the one or more alkene(s) and/or alkyne(s) producing C—C radicals. The C—C radicals may react with further alkene(s) and/or alkyne(s) or may react with the carbon nanotube. The reaction, i.e. the length of the C—C chain may be controlled by the amount of alkene(s) and/or alkyne(s) present in the reaction system. The alkene(s) and/or alkyne(s) may be optionally substituted. The term "optionally substituted" in this respect refers to a group in which none, one, or more than one of the hydrogen atoms has been replaced with one or more group(s) are independently selected from, but not limited to, alkyl, heteroalkyl, haloalkyl, heterohaloalkyl, cycloalkyl, aryl, arylalkyl, heteroaryl, non-aromatic heterocycle, hydroxy, alkoxy, aryloxy, cyano, halo, carbonyl, nitro, silyl, amino, and the like. In the present invention using the term "radical" also encompasses such reaction products of a radical with an alkene and/or alkyne.

Depending on the optionally substituent, the chemical and physical reactivity and properties of the alkene(s) and/or alkyne(s) and thus the final modified carbon nanotubes may be altered. For example, in case the alkene(s) and/or alkyne(s) may have electron-withdrawing groups, such electron-withdrawing groups imparted onto nanotubes after reaction will improve the mobility and on-off ratio of nanotube devices. In one embodiment the alkene(s) and/or alkyne(s) are substituted with one or more electron-withdrawing groups, such as halogens, cyano, carbonyl or nitro groups.

The method of the present invention is for modifying the electrical properties of carbon nanotubes. "Modifying" in this respect means that the different nanotubes which may be present in the mixture may react with the radical produced by the radical initiator or may specifically not react with the radical. Thus, unique species with specific electrical properties from a given nanotube material may be obtained. In one embodiment, metallic species of carbon nanotubes are suppressed, or in other words, in this embodiment, metallic carbon nanotubes are specifically silenced. Illustratively speaking, due to this silencing of metallic carbon nanotubes of the present invention, a device such as a FET using carbon nanotube network as the active channel that made with modified carbon nanotubes according to the invention exhibits high semi-conducting characteristics. The advantage of the current invention is that the modification method is simple, low-cost, scalable, safe, and with high yield and high quality. Generally speaking, the method of the present invention enables the modification of carbon nanotubes according to their electronic properties. In this respect, the term "a composition of carbon nanotubes" as used in the present invention means that at least one carbon nanotube or two or more different carbon nanotubes are present in the system. In one embodiment of the present invention single-walled carbon nanotubes (SWNT) are modified.

The arrangement of the carbon hexagon rings can be characterized by the chiral vector of the carbon nanotubes. Chiral vector is a two dimensional vector (p, q) that is commonly used to describe the geometry of carbon nanotubes (see for example, Wilder et al, Nature 391, 6662, 59-62 (1998)). The values of p and q determine the chirality, or "twist" of the nanotube. The chirality in turn affects properties such as conductance, density, and lattice structure of the carbon nanotubes. Depending on the arrangement of the carbon hexagon rings along the surface of the nanotube as characterized by its chiral vector, carbon nanotubes can be metallic or semiconducting. For example, SWNTs can be metallic when p−q=3r, where r is an integer, and can be semiconducting otherwise. Metallic SWNTs refer to carbon nanotubes with non-zero density of states (DOS) at its Fermi level. The term "density of states" refers to the number of states at an energy level that are available to be occupied, and the term "Fermi level" refers to an energy level with a probability of 50 percent for existence of an electron. Therefore, a SWNT can be metallic when the DOS value at its Fermi level is not zero. Semiconducting SWNTs refer to carbon nanotubes with varying band gaps, wherein the term "band gap" refers to difference in energy between the valance band and the conduction band of a material. Such carbon nanotubes can be separated or enriched by a method according to the present invention. Thus, the method of the present invention allows the enrichment according to electronic properties in order to separate met-SWNT (metallic) from sem-SWNT (semiconducting).

As mentioned above, in one embodiment of the present invention the modification of the electrical properties of carbon nanotubes leads to the suppression of electrical properties of specific carbon nanotubes. For example, in a mixture of semi-conducting SWNT and metallic SWNT the inventive method may lead to the selective suppression of the influence of the metallic SWNT. Therefore, any device made form such a modified mixture may exhibit high semiconducting characteristics.

The modification of the carbon nanotubes, such as SWNT, according to the inventive method may also be size-dependent. Large diameter tubes may be relatively inert to the reaction with a radical initiator. Therefore, in one embodiment of the invention it may be possible to selectively silence the electrical properties of small-diameter tubes without significantly affect large sized tubes. For example, in a mixture of SWNT and MWNT it may be possible to selectively eliminate the electrical influence of SWNT.

In order to achieve the desired modification the composition with the carbon nanotubes is mixed with one or more radical initiator(s) in an organic solvent or a mixture of organic solvents to form a mixture. The modification reaction can be carried out at any suitable temperature as long as the desired (degree of) modification is achieved. The reaction mixture containing the carbon nanotubes and the one or more radical initiator may, in one embodiment, for example be heated to reflux. In other embodiments, the reaction may be carried out at room temperature (25° C.), or at any (elevated) temperature below the boiling point of the used solvent, say, for example between 25° C. and 40° C., or between 25° C. and 50° C., or between 25° C. and 60° C., between 25° C. and 70° C. or between 25° C. and 80° C. If an elevated temperature below the boiling temperature of the used solvent is chosen, this elevated temperature depends of course on the boiling temperature of the solvent. Independent of the chosen reaction temperature, the radical initiator is activated and the obtained modified carbon nanotubes may optionally be isolated subsequently. In one embodiment one or more alkene(s) and/or alkyne(s) are present during the reaction between the radical initiator(s) and the carbon nanotubes.

The mixing can be carried out by standard mixing methods known in the art. Any suitable mixing device may be used, wherein the invention is not limited to a particular device. In one embodiment of the invention the mixing may be carried out, but is not limited to, by sonicating or stirring or shaking the mixture. The mixing time may be chosen according to the used nanotube mixture and/or the used radical initiator. In case of sonication, the mixing time may influence the reaction. For example, in case sonication is too long, the nanotubes may be too short. On the other hand, in case sonication is too long, the reaction may undesirably affect the wanted semi-single walled tubes. A too short reaction time may not significantly eliminate the influence of metallic tubes. This factor can be optimized according to the experimental needs and the nanotubes used. The power of sonication is also a critical factor. If sonication is too strong, the power would make the resulting tubes too short and the temperature too high (a high temperature may affect the selectivity, i.e., semi-CNTs also would react at high temperature). On the other hand, too weak the power would compromise the nanotube dispersion and complete reaction. The determination of the suitable experimental conditions can be done empirically and is within the knowledge of the person of average skill in the art.

In one embodiment of the present invention the mixing is carried out for about 1 to about 60 minutes, such as about 1 to about 30 minutes or about 1 to about 10 minutes. For example, the mixing time may be, but is not limited to, about 1 min, about 2 min, about 3 min, about 4 min, about 5 min, about 6 min, about 7 min, about 8 min, about 9 min, about 10 min, about 15 min, about 20 min, about 25 min, about 30 min, about 35 min, about 40 min, about 45 min, about 50 min, about 55 min, or about 60 min. All mentioned time specifications may be the lower or upper limit of a respective time range. In embodiments where sonication is used as the mixing method, wattage on the sonicator can additionally be varied to achieve a specific level of mixing. A person skilled in the art is able to choose and determine the appropriate mixing time and settings based on the mixing method used to derive a specific weight enrichment of the carbon nanotubes or SWNT.

The mixture of the carbon nanotubes and the radical initiator is made by suspending and/or dissolving the components in a solvent. Any solvent suitable for suspending and/or dissolving the components or a mixture thereof is encompassed by the present invention. In one embodiment, all components may be dissolved and the nanotubes may be well-dispersed. In one embodiment, depending on the compounds being present in the reaction mixture, it may be beneficial to use solvents having a relatively high boiling point. Any desired liquid can be employed, whether an aqueous or non aqueous liquid, an organic liquid (solvent), or a non-polar aprotic, non-polar protic, dipolar protic, dipolar aprotic, or an ionic liquid. Examples of non-polar aprotic liquids include, but are not limited to, hexane, heptane, cyclohexane, benzene, toluene, pyridine, dichloromethane, chloroform, carbon tetrachloride, carbon disulfide, tetrahydrofuran, dioxane, diethyl ether, diisopropylether, ethylene glycol monobutyl ether or tetrahydrofuran. Examples of dipolar aprotic liquids are methyl ethyl ketone, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, and dimethylsulfoxide. Examples of polar protic liquids are water, methanol, ethanol, butyl alcohol, formic acid, dimethylarsinic acid [$(CH_3)_2AsO(OH)$], N,N-dimethylformamide, N,N-diisopropylethylamine, or chlorophenol. Examples of non-polar protic liquids are acetic acid, tert.-butyl alcohol, phenol, cyclohexanol, or aniline. Two illustrative examples of ionic liquids are 1,3-dialkylimidazolium-tetrafluoroborates and 1,3-dialkylimidazolium-hexafluoroborates. In some embodiments the liquid is a polar ionic liquid. Examples of a polar ionic liquid include, but are not limited to, 1-ethyl-3-methylimidazolium tetrafluoroborate, N-butyl-4-methylpyridinium tetrafluoroborate, 1,3-dialkylimidazolium-tetrafluoroborate, 1,3-dialkylimidazolium-hexafluoroborate, 1-ethyl-3-methylimidazolium bis(pentafluoro-ethyl)phosphinate, 1-butyl-3-methylimidazolium tetrakis(3,5-bis(trifluoromethylphenyl)-borate, tetrabutyl-ammonium bis(trifluoromethyl)imide, ethyl-3-methylimidazolium trifluoro-methanesulfonate, 1-butyl-3-methylimidazolium methylsulfate, 1-n-butyl-3-methyl-imidazolium ([bmim]) octylsulfate, and 1-n-butyl-3-methylimidazolium tetrafluoroborate. Examples of a non-polar liquid include, but are not limited to mineral oil, hexane, heptane, cyclohexane, benzene, toluene, dichloromethane, chloroform, carbon tetrachloride, carbon disulfide, dioxane, diethyl ether, diisopropylether, methyl propyl ketone, methyl isoamyl ketone, methyl isobutyl ketone, cyclohexanone, isobutyl isobutyrate, ethylene glycol diacetate, and a non-polar ionic liquid. Examples of a non-polar ionic liquid include, but are not limited to, 1-ethyl-3-methylimidazolium bis[(trifluoromethyl)sulfonyl]amide bis-(triflyl)amide, 1-ethyl-3-methylimidazolium bis[(trifluoromethyl)sulfonyl] amide trifluoro-acetate, 1-butyl-3-methylimidazolium hexafluorophosphate, 1-hexyl-3-methylimidazolium bis(trifluoromethylsulfonyl)imide, 1-butyl-3-methylimidazolium bis(trifluoromethylsul-fonyl)imide, trihexyl(tetradecyl) phosphonium bis[oxalato(2-)]borate, 1-hexyl-3-methyl imidazolium tris(pentafluoroethyl)trifluorophosphate, 1-butyl-3-methyl-imidazolium hexafluorophosphate, tris (pentafluoroethyl)trifluorophosphate, trihexyl(tetradecyl) phosphonium, N"-ethyl-N,N,N',N'-tetramethylguanidinium, 1-butyl-1-methylpyrrolidinium tris(pentafluoroethyl)trifluorophosphate, 1-butyl-1-methylpyrrolidinium bis(trifluoromethylsulfonyl)imide, 1-butyl-3-methyl imidazolium hexafluorophosphate, 1-ethyl-3-methylimidazolium bis(trifluoromethylsulfonyl)imide and 1-n-butyl-3-methylimidazolium.

After mixing the radical initiator is activated. Activation in this respect means that the radical initiator will form the necessary radicals in order to start the reaction with the carbon nanotubes and thus to initiate the modification process. The activation may be carried out by any means which is known in the art and which may be suitable for the respective radical initiator. For example, the activation may be carried out by, but not limited to, thermal heating, light irradiation, redox initiation or sonication.

Thermal heating as activation method may be used in case the respective radical initiator has a dissociation energy that can be easily provided by heating without having any detrimental effect on the overall reaction system. The necessary temperatures will be known to the skilled person.

Sonication may ensure that the carbon nanotubes were homogenously dispersed and sufficiently reacted with the free radicals. Using sonication it may also be possible to mildly elevate the temperature to activate the radical initiators. The initiation and termination of the reactions were simply controlled by the timing of sonication. Sonication may be carried out between about 1 min and about 60 min, such as between about 5 min and about 45 min or between about 10 min and about 30 min, for example between about 20 min to about 30 min. In one embodiment of the invention, the sonication may be carried out at least about 5 min, at least about 10 min, at least about 15 min, at least about 20 min, at least about 25 min, at least about 30 min, at least about 35 min, at least about 40 min, at least about 45 min, at least about 50 min, at least about 55 min or at least about 60 min. All the aforementioned time values may constitute the lower or upper limit of possible time ranges. Light irradiation may be carried out as generally known in the art. For example, such photo initiation occurs when radicals are produced by ultraviolet or visible light irradiation of the reaction system. The skilled person will be aware of the respective radical conditions which may be necessary to activate the radical initiator.

Redox initiation may be carried out as generally known in the art. For example, it is known that many oxidation-reduction reactions produce radicals. An advantage of redox initiation is that that the radical production may occur at reasonable rates over a very wide range of temperatures.

In one embodiment, after activation and carrying out the reaction between the components, the resulting mixture may be present in the form of a supernatant and a precipitated solid. Both the supernatant and the precipitate may contain the nanotube complex which has been formed during the preceding procedure.

In one embodiment of the modified carbon nanotubes may optionally be isolated. The isolation may be carried out by, but is not limited to, filtration, centrifugation and/or settling. The centrifugation may be carried out with generally used conditions. For example, the centrifugation may be carried out, but is not limited to, at least about 5 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, or at least about 55 minutes. In one embodiment the centrifugation is carried out for 1 hour. The centrifugation speed may be, but is not limited to, about 10 Kg, about 20 Kg, about 30 Kg or more. Filtration may be carried out using general filter means, such as for example a polytetrafluoroethylene (PTFE) membrane, a poly-vinyliden-di-fluoride (PVDF) membrane or another commonly used membrane that can be used for filtration purposes. Settling is the process by which particulates settle to the bottom of a liquid and form a sediment. In one embodiment of the present invention the standing time for settling may be between about 0 days and about 4 weeks, such as between about 1 day and about 3 weeks or between about 2 days and about 2 weeks. In one embodiment the standing time is at least about 1 day, at least about 2 days, at least about 3 days, at least about 4 days, at least about 5 days, at least about 6 days, at least about 1 week, at least about 2 weeks, at least about 3 weeks, or at least about 4 weeks. All the aforementioned time specification may constitute the lower or upper limit of possible time ranges.

In one embodiment the resulting modified nanotubes are thoroughly washed with an organic solvent. The organic solvent may be any solvent already mentioned above and which may be suitable for the respective nanotube.

The method of the present invention enables the modification of electrical properties of carbon nanotubes. Depending on the radical initiator used in the inventive process, different carbon nanotubes may be modified. Thus, modification of the used radical initiator may be used to adapt the modification as suitable for the respective nanotubes.

The single-walled carbon nanotube of the invention may also be used as field-effect transistor (FET). Basically, the FET structure involves two metal electrodes designated as "source" and "drain" connected by a semiconducting channel. In conventional devices, the channel is made of Si. In the FET of the present invention the channel is replaced by a sem-single-walled carbon nanotube according to the invention. The FET device based on the radical initiator-modified carbon nanotubes of the present invention have an on-off ratio of at least about 100, such as at least about 500, at least about 100, at least about 5000, at least about 10000, or at least about 15000. Examples of on-off rations include, but are not limited to, about 1000, about 2000, about 3000, about 4000, about 5000, about 6000, about 7000, about 8000, about 9000, about 10000, about 11000, about 12000, about 13000, about 14000 or about 15000. In one embodiment, the radicals may react with the activated metallic carbon nanotube, and suppress the properties of metallic carbon nanotubes, which results in higher on/off ratios. The devices may show higher mobility after reaction with radicals. The FETs obtained with the modified carbon nanotubes of the invention may find application in macroelectronics, printable electronics (such as ink jet printed electronics), and flexible electronics.

The carbon nanotube species, such as SWNTs modified according to the present invention may be used in addition to the above in several applications, for example as electronic component. Examples of further applications of carbon nanotubes include, but are not limited to, conductive and high-strength nanotube/polymer composites, catalysts, transparent electrodes, sensors and nanoelectromechanical devices, additives for batteries, radiation sources, semiconductor devices in general (e.g. transistors, see above), ultracapacitors or interconnects.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Materials

Benzoyl peroxide (BPO) and dimethylformamide (DMF) were obtained from Aldrich and used as purchased. The purified single walled carbon nanotubes used in the experiments (SWeNT®SG 65 tubes) were purchased from SouthWest Nanotechnologies (USA) and they were directly used without further purifications. The preparation of the SWNT suspensions for FET device fabrication comprises of surface modification of SWNTs with BPO in DMF and centrifugation to obtain the supernatants. According to the data sheet of the manufacturer, SWeNT®SG 65 carbon nanotubes have the following typical properties: tube diameter (0.8±0.1 nm), high aspect ratio (1,000), carbon content (>90% by weight), >50% of tubes are (6,5) chirality, >90% of tubes are semiconducting.

Example 1

Preparation of Carbon Nanotubes Modified with BPO

The typical process was as follows: 0.3 mg of SWNTs was dispersed in 30 mL of DMF solution via ultrasonication for 30 min. The ultrasonication was implemented by immersing an ultrasonic probe (Sonics & Materials Inc., Model: VCX 130) into the SWNT solution in ambient. After that, 0.75 mL of DMF solution containing 10 mg/mL BPO was added to 10 mL of obtained SWNT suspension at room temperature, followed by 30 min ultrasonication. After modification with BPO, the suspension was filtered through a 0.25 μm PTFE membrane, followed by repeated washing with DMF and acetone to remove the residuals. Then the powders collected from PTFE membrane were re-dispersed in a 2 wt % of co-surfactants which consists of sodium dodecyl sulfate (SDS) and sodium cholate hydrate (SC) (weight ratio=1:4). The centrifugation was performed at 20000 rpm for 90 min for removal of big bundles in the suspensions. The supernatant was then drawn out from the centrifuge tube, and it was directly used for FET device fabrication.

Figure 2:
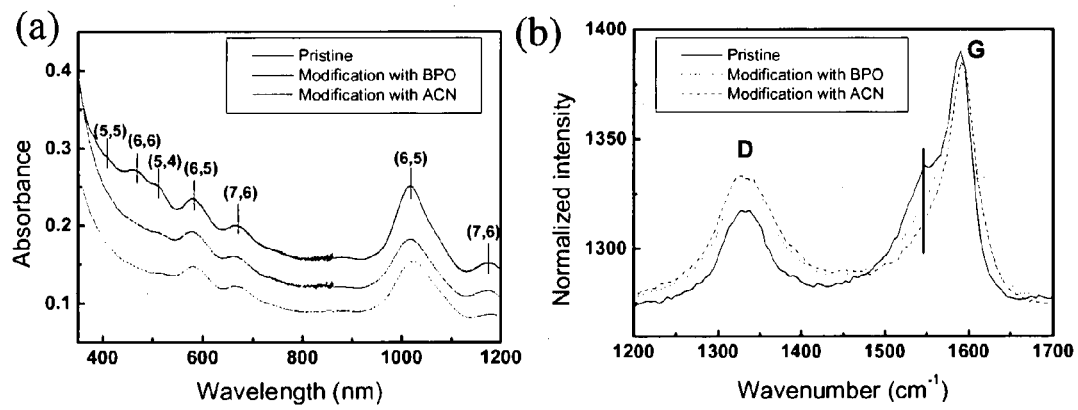
FIG. 2 shows (a) Absorption spectra of the pristine, benzoyl peroxide (BPO)-modified and 1,1'-azobis(cyanocyclohexane) (ACN)-modified SWNTs in DMF. The initial mixing weight ratio of SWNTs and BPO is 1:75, and the weight ratio of SWNTs and ACN is 1:250. (b) Raman D and G bands of the pristine and modified SWNTs.

The reaction between BPO and SWNTs can be schematically seen in FIG. 1. FIG. 2a presents the optical absorption spectrum of the pristine CoMoCat® SWNT ensemble (Table 1) as purchased (different nanotube species are identified as characteristic absorbance peaks), and spectra of the SWNTs modified with BPO in dimethylformamide (DMF) solution. In this connect, it is noted that the SWeNT®SG 65 carbon nano tubes are prepared by the CoMoCat® method (a detailed explanation of the CoMoCat® method can be found on http://www.sigmaaldrich.com/materials-science/nanomaterials/comocat-carbon-nanotubes.html).

TABLE 1

Characteristics of species present in CoMoCat ® SWNTs. The diameter is calculated based on the optimized tight-binding parameters.

| | Species | | | | | |
|---|---|---|---|---|---|---|
| | (5, 4) | (5, 5) | (6, 5) | (6, 6) | (7.5) | (7, 6) |
| Property | semi | Met | semi | met | semi | Semi |
| Diameter (nm) | 0.620 | 0.686 | 0.757 | 0.825 | 0.829 | 0.895 |

Figure 7:
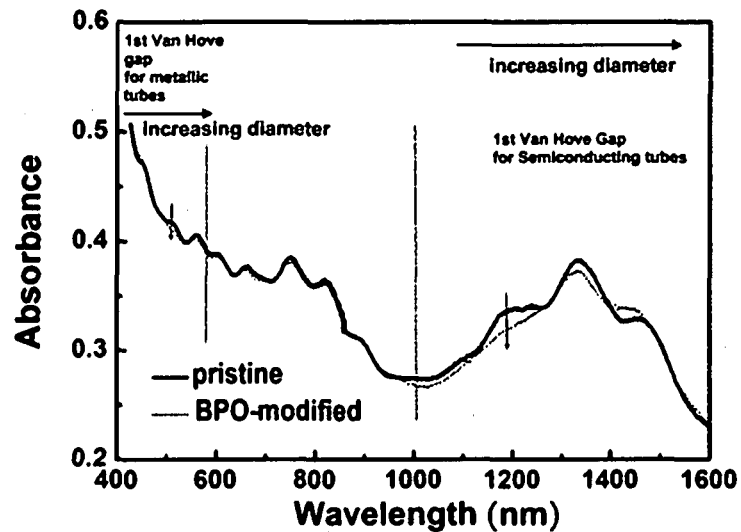
FIG. 7 shows the absorption spectra of the pristine and BPO-modified SWNTs (HiPCO) in 2 wt % SDS/SC (weight ratio=1:4) solutions.
Figure 8:
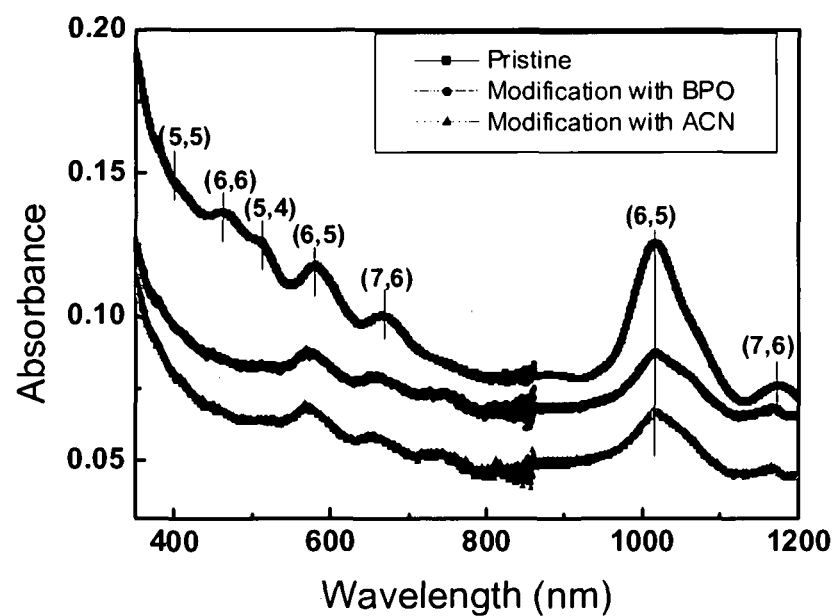
FIG. 8 shows the absorption spectra of the pristine, BPO and ACN-modified SWNTs (CoMoCat 65) in 2 wt % SDS/SC (weight ratio=1:4) solutions after centrifuge at 20000 rpm for 90 min.

Evidently, after reaction with the radicals, all the absorption peaks were reduced. In particular, the peaks of metallic species (5,5), (6,6) and the smallest semiconducting species (5,4) completely disappeared from the spectrum, indicating the preferential suppression of metallic and small tubes. Although the absorption peak from the major semiconducting species (6,5), was also reduced after modification, it still remained dominant due to its abundance. In comparison, BPO modification did not significantly alter the absorption spectrum of HiPCO SWNTs except peak decrease of small nanotubes in the ensemble presumably because HiPCO, which mainly consists of relatively large nanotubes as compared to CoMoCat®, is much less reactive (FIG. 7). In general, the reaction of radicals with the smaller diameter seem to dominate the reaction selectivity [cf. D. B. Mawhinney, V. Naumenko, A. Kuznetsova, J. T. Yates, *J. Am. Chem. Soc.* 2000, 122, 2383-2384; b) A. M. Rao, J. Chen, E. Richter, U.

Schlecht, P. C. Eklund, R. C. Haddon, U. D. Venkateswaran, Y. K. Kwon, D. Tomanek, *Phys. Rev. Lett.* 2001, 86, 3895-3898; c) G. Y. Zhang, P. F. Qi, X. R. Wang, Y. R. Lu, X. L. Li, R. Tu, S. Bangsaruntip, D. Mann, L. Zhang, H. J. Dai, *Science* 2006, 314, 974-977]. Meanwhile, the selectivity with the metallic tubes may also play a role.

Preparation of Carbon Nanotubes FETs

The SWNT FETs (SNFETs) were fabricated by drop-casting the obtained SWNT suspension on a bottom contact device geometry, where 100 nm thick of Au electrodes (as Au-SWNT contact) were patterned on top of $SiO_2$/Si substrates using standard lithography techniques. The gate dielectrics $SiO_2$ is 300 nm thick. The geometry of the investigated devices is 50 μm in channel length and 25 μm in channel width. For the drop-cast procedure, 25 μL of SWNT suspension was dropped onto the devices, followed by drying at room temperature and rinsing of de-ionized water. The procedure was repeated until the BPO functionalized SWNT density is high enough to form a percolation path or to the desired current level.

A confocal Raman microscope (WITec CRM200) equipped with 488 nm of laser was used for Raman measurements. Optical absorption measurements were performed in a Perkin Elmer Lambda 9 UV-Vis-Nir spectrometer. All electrical measurements were carried out in ambient using a Kiethley semiconductor parameter analyzer, model 4200-SCS. Atomic force microscopy (AFM) measurement was carried out using an Asylum Research MFP-3D system to image the SWNTs. The scanning electron microscope (SEM) image was taken using a Hitachi Ultra-high-Resolution S-4800 scanning electron microscope. Transmission electron microscope (TEM) was done by an FEI Philips Tecnai 20 Electron Microscope. X-Ray photoelectron spectroscopy (XPS) analysis was used Al Ka radiation in an ESCA Lab 220I-XL instrument.

Characterization and Discussion

To confirm the effective and preferential suppression of metallic tubes in the CoMoCat® SWNT ensemble, Raman spectra of the pristine and BPO-modified tubes were compared (FIG. 1c). It was observed that the longitudinal G-bands from metallic-species at ~1544 $cm^{-1}$ were reduced after modification, indicating the preferential suppression of metallic-species. Meanwhile, the D bands of SWNTs were enhanced after modification due to destruction of graphitic lattice (cf. M. S Strano, C. A. Dyke, M. L. Usrey, P. W. Barone, M. J. Allen, H. W. Shan, C. Kittrell, R. H. Hauge, J. M. Tour, R. E. Smalley, Science 2003, 301, 1519-1522; b) D. McIntosh, V. N. Khabashesku, E. V. Barrera, *J. Phys. Chem. C* 2007, 111, 1592-1600; c) H. Q. Peng, P. Reverdy, V. N. Khabashesku, J. L. Margrave, *Chem. Comm.* 2003, 362-363) induced by sidewall functionalizations.

Figure 3:
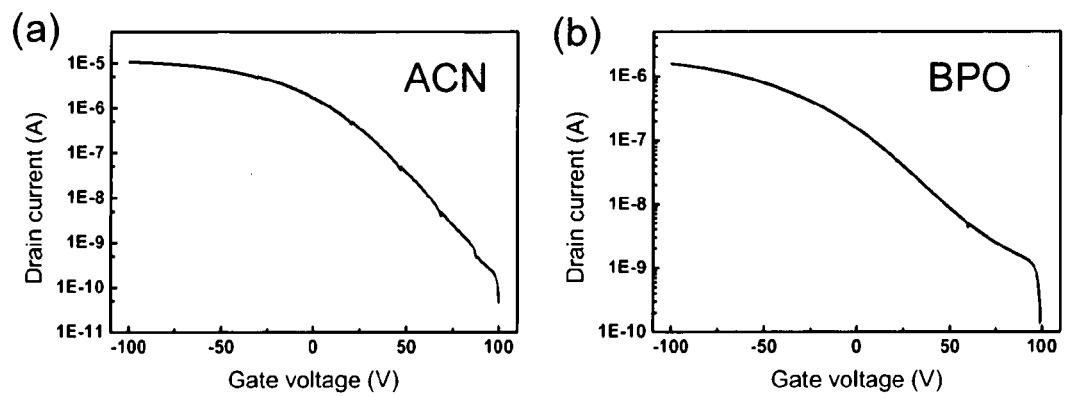
FIG. 3 shows transfer characteristics of the bottom-gated thin-film transistors drop-casted from ACN-modified (a) and BPO-modified (b) SWNT suspensions. The channel length and width are 50 μm and 25 μm, respectively
Figure 4:
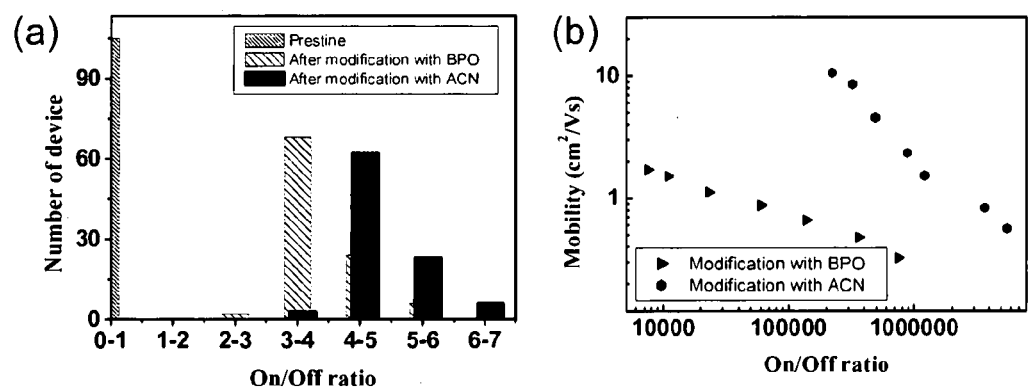
FIG. 4 shows the histogram of the on-off ratios of the devices fabricated using the pristine and functionalized SWNTs. (b) Relation between on-off ratio and effective hole mobility.

Thin-film field-effect transistor (FET) devices based on BPO-modified SWNTs were fabricated by simple drop-casting method and electrically characterized. FIG. 3b shows the transfer curve (drain current $I_d$ versus gate voltage $V_g$) of a typical transistor device. The effective hole mobility of this device is around 1.7 $cm^2$/Vs and its on-off ratio is >11400. As revealed by AFM imaging, the thickness of the deposited SWNT film is ~40 nm (not shown). FIG. 3b shows the histogram of the on-off ratios of the devices made with pristine or BPO-modified SWNTs. The statistics was obtained from the drop-cast devices without deliberate control on film thickness, i.e., the SWNT containing droplets were applied to the channel area until the resistance of the device became smaller than 10 MΩ. Only very low on-off ratios (ranging from 1.2 to 10) were obtained from the devices made by the pristine CoMoCat® SWNTs, implying that electrical property of the percolative network of pristine SWNTs is determined by the minor metallic species. In drastic contrast, the devices from the BPO-modified SWNTs were dominantly semiconducting, with on-off ratios higher than 1000 (98 out of 100 devices). Only 2 devices were found to have relatively low on-off ratios (a few hundreds). Such electrical characterization further supported our conclusion that the metallic species were electrically silenced by chemical modification. In an experiment shown in FIG. 4b, the device mobility increased while adding more SWNTs to the channel area, whereas the device on-off ratio decreased at the same time. Therefore, there is a trade-off between the mobility and the on-off ratio, presumably due to the residual metallic tubes.

Figure 9:
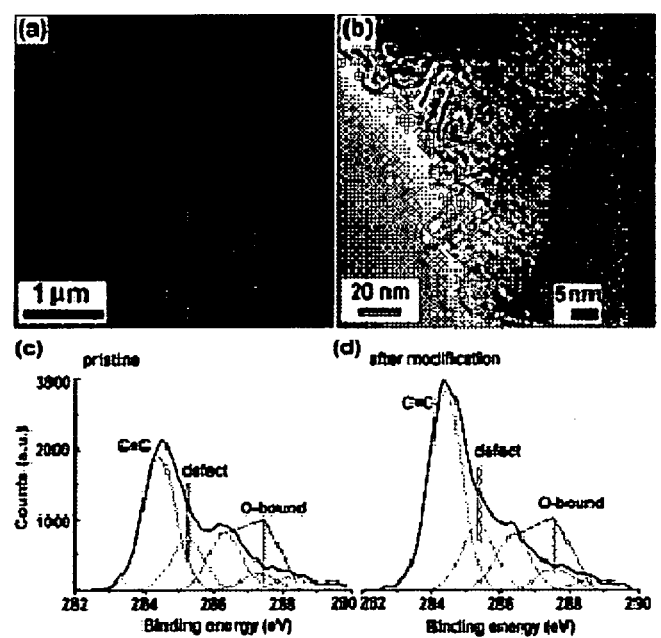
FIG. 9 shows (a) SEM, (b) TEM image of the BPO-modified CoMoCat® 65 SWNTs ($m_{CNT}$:$m_{BPO}$=1:75). Inset of (b) is the high resolution image showing the presence of surface coating. XPS spectra of the (c) pristine and (d) BPO-modified SWNTs around the C1s binding energy.

FIGS. 9a and 9b presents a typical scanning electron microscopic (SEM) and a transmission electron microscopic (TEM) images of BPO-modified SWNTs, respectively. Under both SEM and TEM, the BPO-modified SWNT-net appeared like a composite material covered by a layer of coatings. Even from high-resolution TEM (inset of FIG. 9b), it is not possible to visually determine whether the surface coatings were chemically bonded to or physically blended with SWNTs. Nonetheless, the largely enhanced semiconducting characteristics of the devices made by the BPO-modified SWNTs (FIGS. 3b and 4a) and its Raman spectrum (FIG. 2b) strongly suggest that the electronic structure of the metallic tubes was deteriorated by the chemical groups imparted onto the SWNT surfaces, while the semiconducting tubes, particularly (6,5) tubes whose adsorption peak is prominent after modification (FIG. 2a), were less affected.

Figure 5:
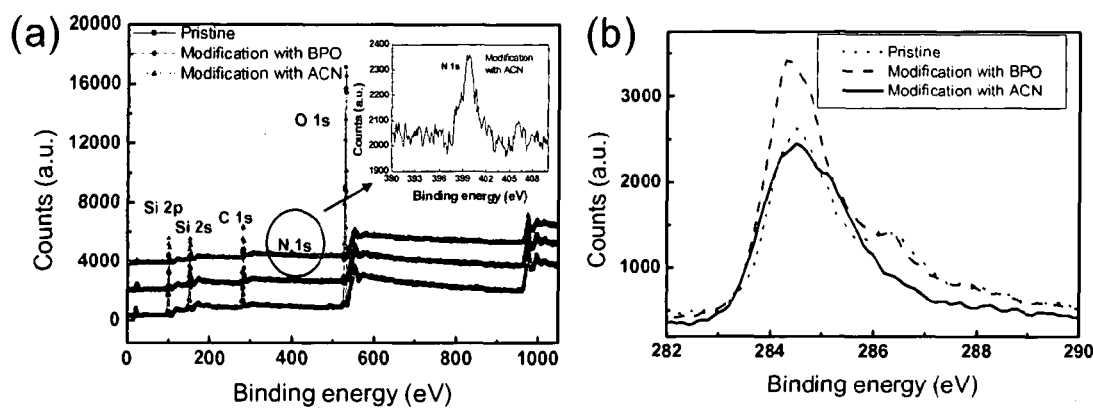
FIG. 5 shows (a) Wide scanning XPS spectra of CoMoCat® 65 SWNTs before and after modification with BPO and ACN, respectively. Inset shows the high-resolution N is peak from ACN-modified SWNTs. (b) XPS spectra for the pristine and functionalized SWNTs around the C1s binding energy.
Figure 6:
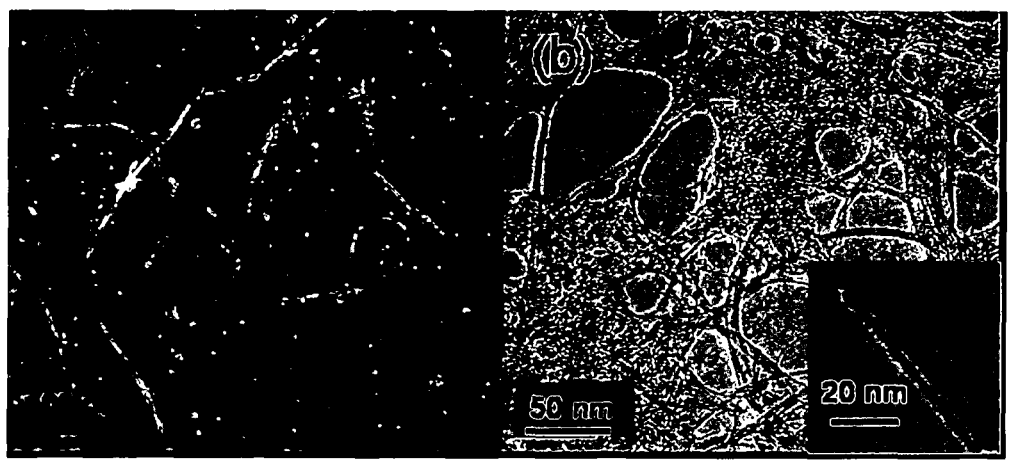
FIG. 6. (a) SEM and (b) TEM image of the ACN-modified CoMoCat® 65 SWNTs.

FIGS. 9c and 9d show the X-Ray photoelectron spectroscopy (XPS) spectra for the pristine and BPO-modified SWNTs around the C1s binding energy. In the wide range of XPS spectra, only difference between these samples is the profile of SWNT species (FIG. 5a). Curve-fitting the XPS spectra in FIGS. 9a and 9b reveals that the peak intensity of the $sp^2$ carbon tubes at 284.3 eV was relatively increased after BPO-modification. This observation is consistent with the notion that the coatings on SWNTs are phenyl ($sp^2$ carbon) group-containing chemical groups introduced by BPO derived radicals.

The selective suppression of metallic species in CoMoCat® SWNTs is not unique to the peroxide initiator BPO. The azo-type initiator such as 1,1'-azobis(cyanocyclohexane) (ACN; chemical structure shown in FIG. 1) also exhibits similar selectivity. FIG. 2a shows the absorption spectra of the ACN-modified SWNTs in DMF solutions, where the metallic species are clearly suppressed. FIG. 3a demonstrates the transfer curve of a FET drop-cast from ACN-modified SWNTs and its on-off and carrier mobility go up to $10^5$ and 4.2 $cm^2$/Vs, respectively. In summary, the radical initiator BPO or ACN allows for controllable release of radicals activated by probe-sonication, and the decomposed radicals preferentially react with small diameter SWNTs (most of nanotubes obtained by the CoMoCat® method are <1 nm) and metallic SWNTs. Using this strategy, semiconducting thin-film nanotube transistors with high on-off ratio and high mobility (up to 4.2 $cm^2$/Vs) can be readily made with high yield by simple and fast solution-based processes. This method promises applications in high-performance and low-cost macroelectronics.

Example 2

Preparation of Carbon Nanotubes Modified with ACN

CNT powders 0.3 mg were dispersed in 30 mL organic solutions (such as DMF) with the aid of sonication to debundle the CNTs. It is noted that the aggregation of the CNTs will result in poor selectivity in the subsequent reaction. 0.75 mL of radical initiator ACN solution (10 mg/mL in DMF) was added into the solution, followed by dissociation of the initiators using mild sonication (30 min). The radical reaction is performed in ambient condition (room temperature). After modification with ACN, the suspension was filtered through a 0.25 μm PTFE membrane, followed by repeated washing with DMF and acetone to remove the residuals. Then the powders collected from PTFE membrane were re-dispersed in a 2 wt % of co-surfactants which consists of sodium dodecyl sulfate (SDS) and sodium cholate hydrate (SC) (weight ratio=1:4). It is noted that the powders recovered from the PTFE membrane can be dispersed to organic solvents (such as DMF or NMP) depending on the substrate compatibility of the solution or the subsequent device fabrication process. SDS/SC co-surfactant solution is only one of the options.

Preparation of Carbon Nanotubes FETs

The re-dispersed solution can be directly used to fabricate transistor devices by drop-casting or ink-jet printing technique.

The invention claimed is:

1. A method for enriching specific species of carbon nanotubes according to their electronic properties and/or their diameter, comprising modifying the electrical properties of carbon nanotubes by subjecting a composition of carbon nanotubes to one or more radical initiator(s), wherein the modification is carried out in the presence of one or more alkene(s) or one or more alkyne(s) or mixtures thereof to produce C—C radicals, wherein the alkene or alkyne is substituted with one or more electron-withdrawing groups, and wherein the specific species of carbon nanotubes to be enriched comprises single-walled semiconducting carbon nanotubes;

wherein the method comprises:
mixing the composition of carbon nanotubes with the one or more radical initiator(s) in an organic solvent or a mixture of organic solvents to form a mixture, wherein the radical initiator is selected from the group consisting of organic peroxides, inorganic initiators, halogen-containing compounds and mixtures thereof;
activating the one or more radical initiator(s) to form radicals;
reacting the carbon nanotubes with the radicals, wherein the radicals preferably react with those species of carbon nanotubes different from the specific species of carbon nanotubes to be enriched; and
separating the modified carbon nanotubes from the unmodified carbon nanotubes, thereby enriching the specific species of carbon nanotubes.

2. The method as claimed in claim 1, wherein the carbon nanotubes are a mixture of nanotubes with different electronic properties and/or sizes.

3. The method of claim 1, wherein the modified carbon nanotubes comprise metallic carbon nanotubes.

4. The method of claim 1, wherein modification of electronic properties allowing the enrichment of the specific species of carbon nanotubes further allows suppressing the electronic properties of metallic single-walled carbon nanotubes.

5. The method of claim 1, wherein the organic peroxides are selected from the group consisting of methyl ethyl ketone peroxide, benzoyl peroxide, acetone peroxide, pinane hydroperoxide, cumene hydroperoxide, tert-butyl hydroperoxide (TBHP), 1,1-bis(tert-amylperoxy)cyclohexane, 1,1-bis(tert-butylperoxy)-3,3,5-trimethylcyclohexane, 1,1-bis(tert-butylperoxy)cyclohexane, 2,2-bis(tert-butylperoxy)butane, 2,4-pentanedione peroxide, 2,5-bis(tert-butylperoxy)-2,5-dimethylhexane, 2,5-di(tert-butylperoxy)-2,5-dimethyl-3-hexyne, 2-butanone peroxide, di-tert-amyl peroxide, tert-butylperoxy octoate, tert-butylperoxy neodecanoate, tert-butylperoxy isobutarate, dicumyl peroxide, lauroyl peroxide, tert-amylperoxy pivalate, tert-butylperoxy pivalate, tert-butyl peroxyacetate, tert-butyl peroxybenzoate, tert-butylperoxy 2-ethylhexyl carbonate and mixtures thereof.

6. The method of claim 1, wherein the inorganic initiators are selected from the group consisting of hydrogen peroxide, ammonium persulfate, hydroxymethanesulfinic acid monosodium salt dihydrate, potassium persulfate, sodium persulfate and mixtures thereof.

7. The method of claim 1, wherein the halogen-containing molecules are selected from the group consisting of fluorine- and chlorine-containing molecules.

8. The method of claim 1, wherein mixing the composition of carbon nanotubes is carried out by sonicating or stirring or shaking the mixture.

9. The method of claim 1, wherein the radical initiators are activated by thermal heating, light irradiation, redox initiation and/or sonication.

10. The method of claim 1, wherein the organic solvent is selected from the group consisting of hexane, heptane, cyclohexane, benzene, toluene, pyridine, dichloromethane, chloroform, carbon tetrachloride, carbon disulfide, tetrahydrofuran, dioxane, diethyl ether, diisopropylether, ethylene glycol monobutyl ether, methyl ethyl ketone, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, dimethylsulfoxide water, methanol, ethanol, butyl alcohol and formic acid.

11. The method of claim 1, wherein the separation is carried out by filtration, centrifugation and/or settling.

12. The method of claim 1, wherein the reaction is carried at room temperature.

13. The method of claim 1, wherein the separated carbon nanotubes are washed with an organic solvent.

* * * * *